(12) United States Patent
Valsan et al.

(10) Patent No.: US 9,968,285 B2
(45) Date of Patent: May 15, 2018

(54) MULTISPECTRAL MEDICAL IMAGING DEVICES AND METHODS THEREOF

(71) Applicant: CHRISTIE DIGITAL SYSTEMS USA, INC., Cypress, CA (US)

(72) Inventors: Gopal Valsan, Brampton (CA); Sina Zarei Mahmoodabadi, Waterloo (CA); Robert Benjamin Wagner, Kitchener (CA); David Priest, Cambridge (CA); Robert Amelard, Waterloo (CA)

(73) Assignee: CHRISTIE DIGITAL SYSTEMS USA, INC., Cypress ( * ) Notice: Subject to any disclaimer, the term of this patent is extended or adjusted under 35 U.S.C. 154(b) by 445 days.

(21) Appl. No.: 14/341,103

(22) Filed: Jul. 25, 2014

(65) Prior Publication Data
US 2016/0022181 A1    Jan. 28, 2016

(51) Int. Cl.
*A61B 5/1455* (2006.01)
*A61B 5/02* (2006.01)
(Continued)

(52) U.S. Cl.
CPC ...... *A61B 5/14551* (2013.01); *A61B 5/02007* (2013.01); *A61B 5/0261* (2013.01);
(Continued)

(58) Field of Classification Search
CPC ............ A61B 5/14551; A61B 5/02416; A61B 5/14552; A61B 5/7207; A61B 5/4818; A61B 5/1455; A61B 5/14553; A61B 5/72
See application file for complete search history.

(56) References Cited

U.S. PATENT DOCUMENTS

| 4,426,726 A | 1/1984 | Cheetham |
| 6,021,210 A * | 2/2000 | Camus ................ A61B 3/1216 348/370 |

(Continued)

FOREIGN PATENT DOCUMENTS

| AU | 2005327078 A1 | 8/2006 |
| CN | 202078301 U | 12/2011 |

(Continued)

OTHER PUBLICATIONS

Bashi, et al., "Use of a multi-spectral camera in the characterization of skin wounds," Optics Express, vol. 18, No. 4, pp. 3244-3257, Feb. 15, 2010.

(Continued)

*Primary Examiner* — Eric Winakur
*Assistant Examiner* — Chu Chuan (J J) Liu
(74) *Attorney, Agent, or Firm* — Perry + Currier Inc.

(57) ABSTRACT

A multispectral medical imaging device includes illumination devices arranged to illuminate target tissue. The illumination devices emit light of different near-infrared wavelength bands. The device further includes an objective lens, a near-infrared image sensor positioned to capture image frames reflected from the target tissue, and a visible-light image sensor positioned to capture image frames reflected from the target tissue. A processor is configured to modulate near-infrared light output of the plurality of illumination devices to illuminate the target tissue. The processor is further configured to determine reflectance intensities from the image frames captured by the near-infrared image sensor and to generate a dynamic tissue oxygen saturation map of the target tissue using the reflectance intensities. The device further includes an output device connected to the processor for displaying the dynamic tissue oxygen saturation map.

37 Claims, 11 Drawing Sheets

(51) Int. Cl.
*A61B 5/00* (2006.01)
*A61B 5/026* (2006.01)

(52) U.S. Cl.
CPC ............ *A61B 5/1455* (2013.01); *A61B 5/489* (2013.01); *A61B 5/70* (2013.01); *A61B 5/7207* (2013.01); *A61B 5/742* (2013.01); *A61B 2576/02* (2013.01)

(56) References Cited

U.S. PATENT DOCUMENTS

| | | | |
|---|---|---|---|
| 6,503,195 | B1 | 1/2003 | Keller et al. |
| 6,640,130 | B1 | 10/2003 | Freeman et al. |
| 6,640,132 | B1 | 10/2003 | Freeman et al. |
| 6,826,424 | B1 | 11/2004 | Zeng et al. |
| 6,937,885 | B1 | 8/2005 | Lewis et al. |
| 6,985,172 | B1* | 1/2006 | Rigney .............. G06K 9/00335 348/149 |
| 7,147,371 | B2 | 12/2006 | Hecker |
| 7,342,658 | B2 | 3/2008 | Kowarz et al. |
| 7,460,248 | B2 | 12/2008 | Kurtz et al. |
| 7,791,008 | B2 | 9/2010 | Hargrove et al. |
| 8,224,425 | B2 | 7/2012 | Freeman et al. |
| 8,371,751 | B2* | 2/2013 | Vazquez .............. A61B 5/1128 378/206 |
| 8,644,911 | B1 | 2/2014 | Panasyuk et al. |
| 8,681,126 | B2* | 3/2014 | Keam ................... G06F 3/0383 178/18.11 |
| 8,743,201 | B2 | 6/2014 | Huang et al. |
| 2004/0236229 | A1* | 11/2004 | Freeman .............. A61B 5/0059 600/474 |
| 2005/0049467 | A1* | 3/2005 | Stamatas .............. A61B 5/0059 600/315 |
| 2005/0131284 | A1* | 6/2005 | Grinvald ............ A61B 5/14555 600/323 |
| 2006/0241495 | A1* | 10/2006 | Kurtz ................... A61B 5/0059 600/476 |
| 2007/0024946 | A1* | 2/2007 | Panasyuk .............. A61B 5/0059 359/253 |
| 2008/0139908 | A1 | 6/2008 | Kurth |
| 2009/0091554 | A1 | 4/2009 | Keam |
| 2009/0245601 | A1* | 10/2009 | Cohen .................... A61B 5/489 382/128 |
| 2010/0056928 | A1 | 3/2010 | Zuzak et al. |
| 2010/0069758 | A1 | 3/2010 | Barnes et al. |
| 2010/0185100 | A1* | 7/2010 | Urban .................. A61B 5/0059 600/475 |
| 2011/0012866 | A1 | 1/2011 | Keam |
| 2011/0144462 | A1 | 6/2011 | Lifsitz et al. |
| 2012/0071765 | A1* | 3/2012 | Chinnock ............ A61B 5/0075 600/476 |
| 2012/0130258 | A1* | 5/2012 | Taylor ...................... A61B 3/13 600/476 |
| 2012/0277559 | A1 | 11/2012 | Kohl-Bareis et al. |
| 2013/0012794 | A1* | 1/2013 | Zeng .................. A61B 1/00186 600/328 |
| 2013/0250123 | A1* | 9/2013 | Zhang .................. G06T 7/0028 348/164 |
| 2013/0322729 | A1* | 12/2013 | Mestha ..................... A61B 5/02 382/134 |
| 2014/0046152 | A1 | 2/2014 | Bechtel et al. |
| 2014/0187968 | A1 | 7/2014 | Pinho |
| 2014/0240464 | A1* | 8/2014 | Lee ......................... G01S 17/08 348/47 |
| 2014/0275880 | A1* | 9/2014 | Verkruijsse ........ A61B 5/14552 600/323 |

FOREIGN PATENT DOCUMENTS

| | | | |
|---|---|---|---|
| CN | 102473061 A | 5/2012 | |
| CN | 102893137 A | 1/2013 | |
| CN | 103505182 A | 1/2014 | |
| CN | 103892844 A | 7/2014 | |
| WO | 2006102640 A2 | 9/2006 | |
| WO | 2010001280 A1 | 1/2010 | |
| WO | WO 2014012946 A1 * | 1/2014 | ............. H04N 5/332 |

OTHER PUBLICATIONS

D. Firmenich, et al., "Multispectral Interest Points for Rgb-Nir Image Registration," 2011.
E. Coiras, et al., "A Segment-based Registration Technique for Visual-IR Images," 2000.
G.A. Bilodeau, et al., "Visible and infrared image registration using trajectories and composite foreground images," Preprint submitted to Image and Vision Computing, Jun. 8, 2010.
H. Zhou, et al., "Feature-preserving Artifact Removal from Dermoscopy Images," 2008.
Hayden, et al., "Oxygenation and blood volume changes in flaps according to near-infrared spectrophotometry," Abstract, Arch Otolaryngol Head Neck Surg., Dec. 1996; 122(12): 1347-51.
Jungong Han, et al., "Visible and Infrared Image Registration Employing Line-Based Geometric Analysis," Muscle 2011, LNCS 7252, pp. 114-125, 2012.
Kainerstorfer JM et al., "Direct curvature correction for noncontact imaging modalities applied to multispectral imaging." Journal of Biomedical Optics 15(4): 046013-046013-14, Jul./Aug. 2010.
M. Hammer, et al., "A simple algorithm for in vivo ocular fundus oximetry compensating for non-haemoglobin absorption and scattering," Physics in Medicine and Biology, 47 (2002) N233-N238.
M.S. Alam, et al., "Infrared Image Registration and High-Resolution Reconstruction Using Multiple Translationally Shifted Aliased Video Frames," IEEE Transactions on Instrumentation and Measurement, vol. 49, No. 5, Oct. 2000.
Mahajan, et al., "Artefact Removal and Contrast Enhancement for Dermoscopic Images Using Image Processing Techniques," International Journal of Innovative Research in Electrical, Electronics, Instrumentation and Control Engineering, vol. 1, Issue 9, Dec. 2013.
Nguyen, et al., "Segmentation of light and dark hair in dermoscopic images: a hybrid approach using a universal kernel," SPIE vol. 7623, 76234N, pp. 76234N-1-76234N-4, 2010.
O. Cordon, et al., "Image registration with iterated local search," J Heuristics (2006) 12: 73-94.
S.G. Kong, et al., "Multiscale Fusion of Visible and Thermal IR Images for Illumination-Invariant Face Recognition," International Journal of Computer Vision 71(2), 215-233, 2007.
S.R. Patel, et al., "A Prototype Hyperspectral System With a Tunable Laser Source for Retinal Vessel Imaging," Investigative Ophthalmology & Visual Science, vol. 54, No. 8, pp. 5163-5168, Aug. 2013.
Shah et al., "Noninvasive functional optical spectroscopy of human breast tissue," Proceedings of the National Academy of Sciences, vol. 98, No. 8, pp. 4420-4425, www.pnas.orgycgiydoiy10.1073ypnas.071511098, Apr. 10, 2001.
Snikkers, Marco, "New advances in multispectral imaging: 2 methods applied in a biomedical test", Ocean Optics EMEA Microsoft Office PowerPoint 2007 Presentation Created Jun. 15, 2010.
Sultana, et al., "Removal of artifacts from dermatoscopic images," IEEE, 2014.
T. Chakravorty, et al., "Automatic Image Registration in Infrared-Visible Videos using Polygon Vertices," Mar. 17, 2014.
Wariar, et al., "A modular NIRS system for clinical measurement of impaired skeletal muscle oxygenation," Journal of Applied Physiology 88, pp. 315-325, 2000.
Yunlong Sheng et al., "Visible/IR Battle Field Image Registration using Local Hausdorff Distance," 1999.
Zonios, et al., "Skin Melanin, Hemoglobin, and Light Scattering Properties can be Quantitatively Assessed In Vivo Using Diffuse Reflectance Spectroscopy," Journal of Investigative Dermatology, vol. 117, No. 6, pp. 1452-1457, Dec. 6, 2001.
Extended European Search Report dated Dec. 23, 2015 for European Patent Application No. 15178385.9.

* cited by examiner

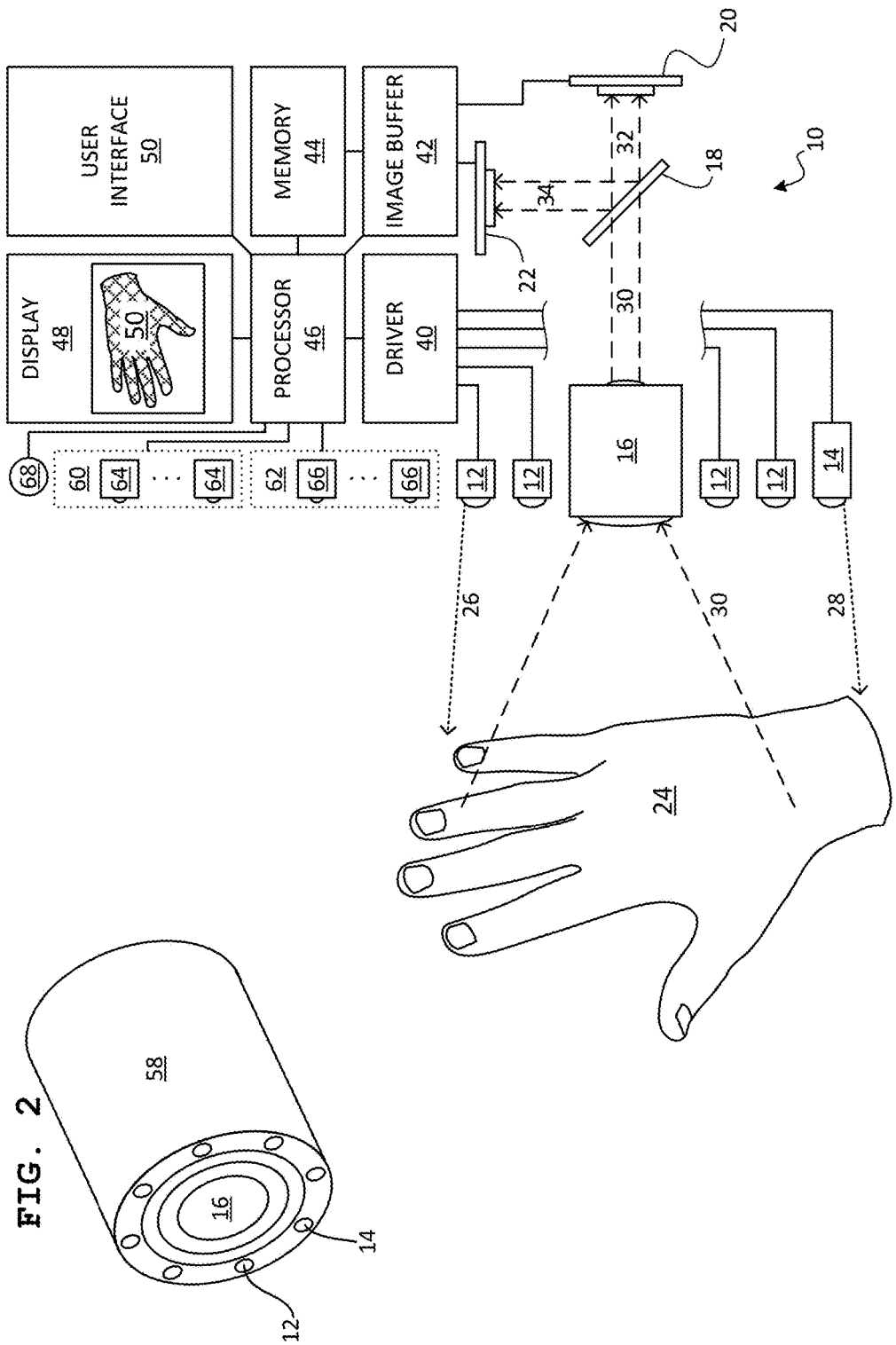

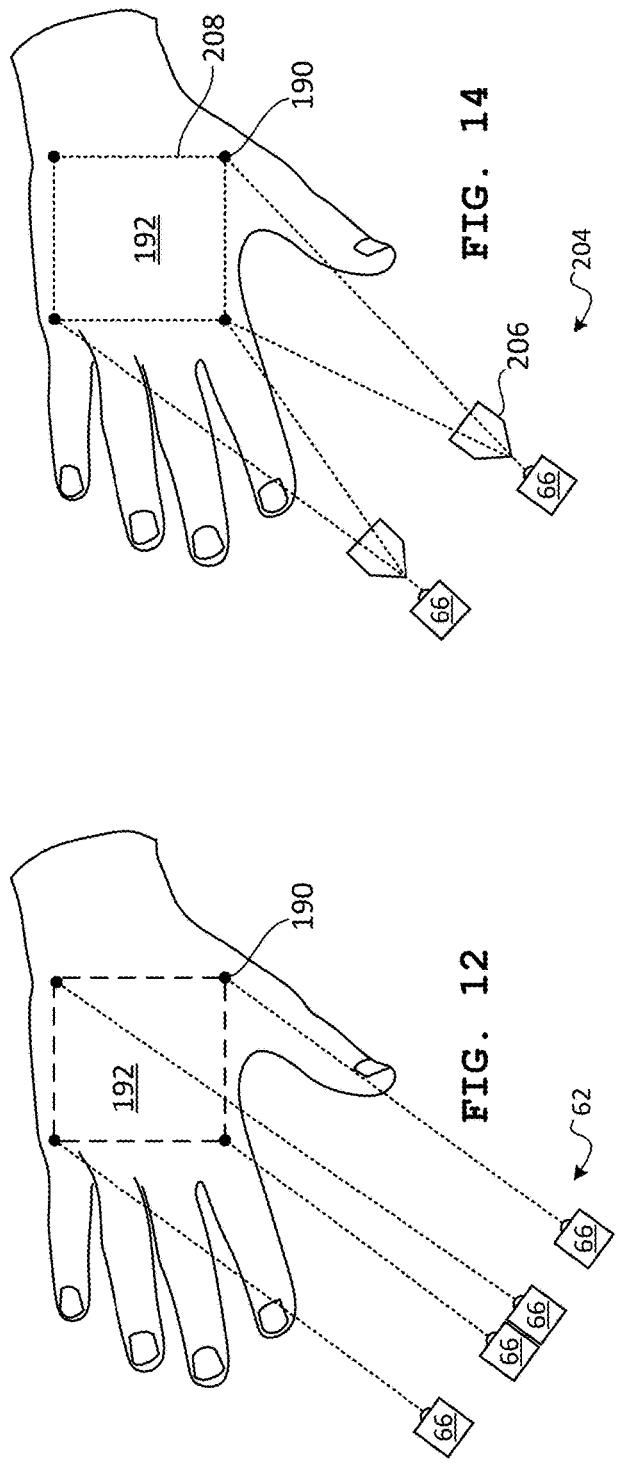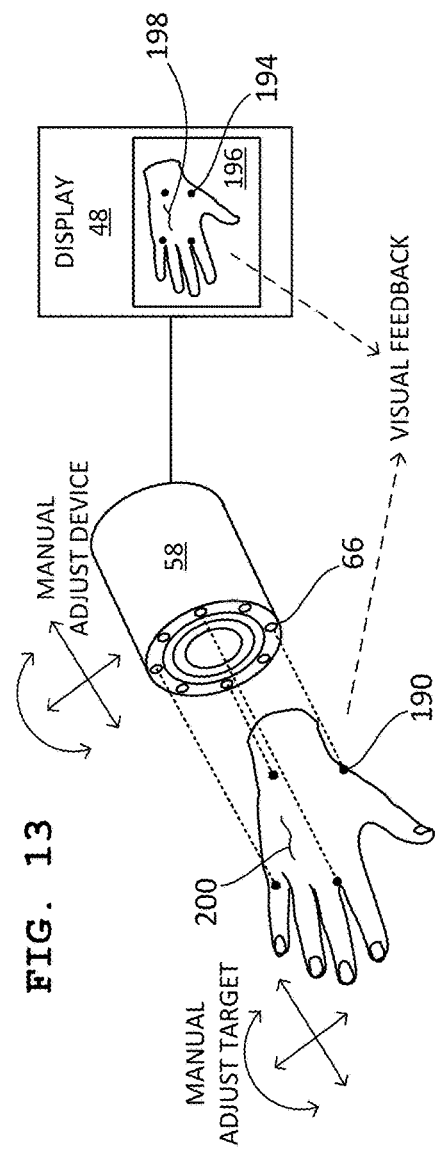

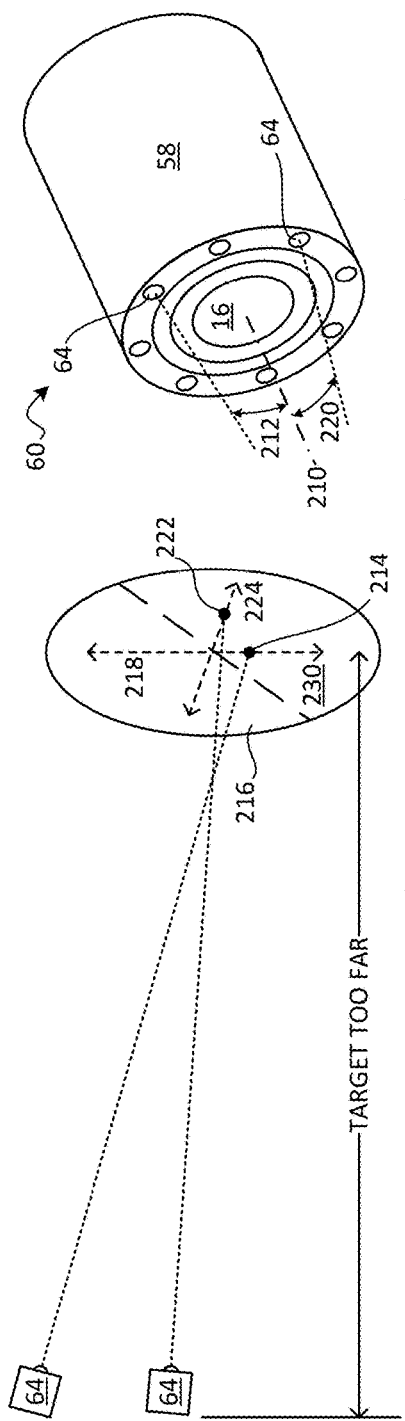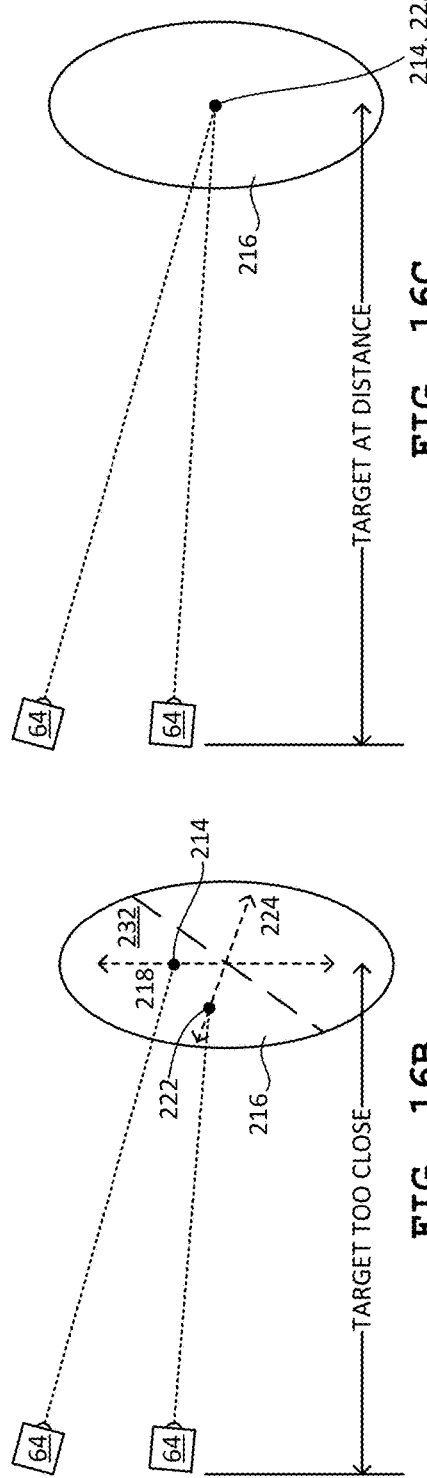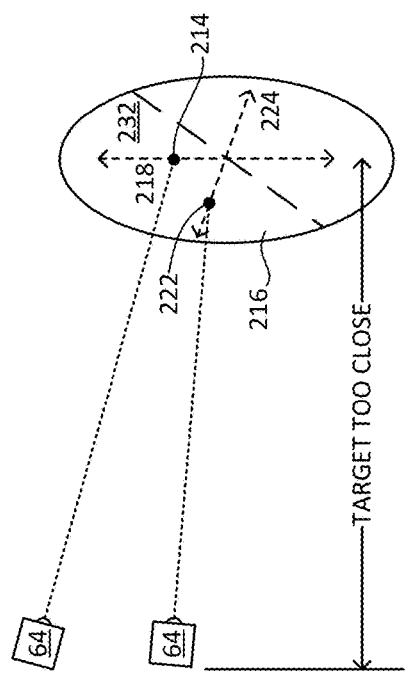

MULTISPECTRAL MEDICAL IMAGING DEVICES AND METHODS THEREOF

FIELD

This disclosure relates to medical imaging, more specifically, to multispectral medical imaging devices and methods thereof.

BACKGROUND

Multispectral medical imaging is known to be used to measure oxygenation of blood vessels and tissue. It is an important tool. Quantified oxygenation data can assist medical professionals in providing better patient care.

State-of-the-art techniques for multispectral medical imaging suffer from various drawbacks. Some tools only offer the ability to make spot measurements on small areas of tissue. Other tools are only capable of providing still images or low frame-rate moving images, which can make clinical assessment more difficult. Some tools suffer from the lack of a convenient way to accurately and repeatedly position and aim towards a target area on the patient. In addition, it is often the case that ambient conditions, such as overhead lighting, and patient particulars, such as skin tone, detrimentally affect measurements.

There is a need for improvement in the field of multispectral medical imaging.

SUMMARY

According to an aspect of the present invention, a multispectral medical imaging device includes a plurality of illumination devices arranged to illuminate a target tissue. The illumination devices are configured to emit light of different near-infrared wavelength bands. The device further includes an objective lens, a near-infrared image sensor positioned to capture image frames reflected from the target tissue through the objective lens, and a visible-light image sensor positioned to capture image frames reflected from the target tissue through the objective lens. A processor is connected to the near-infrared image sensor, the visible-light image sensor, and the plurality of illumination devices. The processor is configured to modulate near-infrared light output of the plurality of illumination devices to illuminate the target tissue. The processor is further configured to determine reflectance intensities from the image frames captured by the near-infrared image sensor and to generate a dynamic tissue oxygen saturation map of the target tissue using the reflectance intensities. The device further includes an output device connected to the processor for displaying the dynamic tissue oxygen saturation map.

BRIEF DESCRIPTION OF THE DRAWINGS

The drawings illustrate, by way of example only, embodiments of the present invention.

FIG. 1 is a block diagram of a multispectral medical imaging device.

FIG. 2 is a perspective diagram of a portion of the multispectral medical imaging device including a housing.

FIG. 12 is a schematic diagram of a laser framing array.

FIG. 13 is a schematic diagram showing use of the laser framing array.

FIG. 14 is a schematic diagram of another laser framing array.

FIG. 15 is a perspective diagram of a laser positioning array.

FIGS. 16A-16C are diagrams showing use of the laser positioning array.

DETAILED DESCRIPTION

Figure 3:
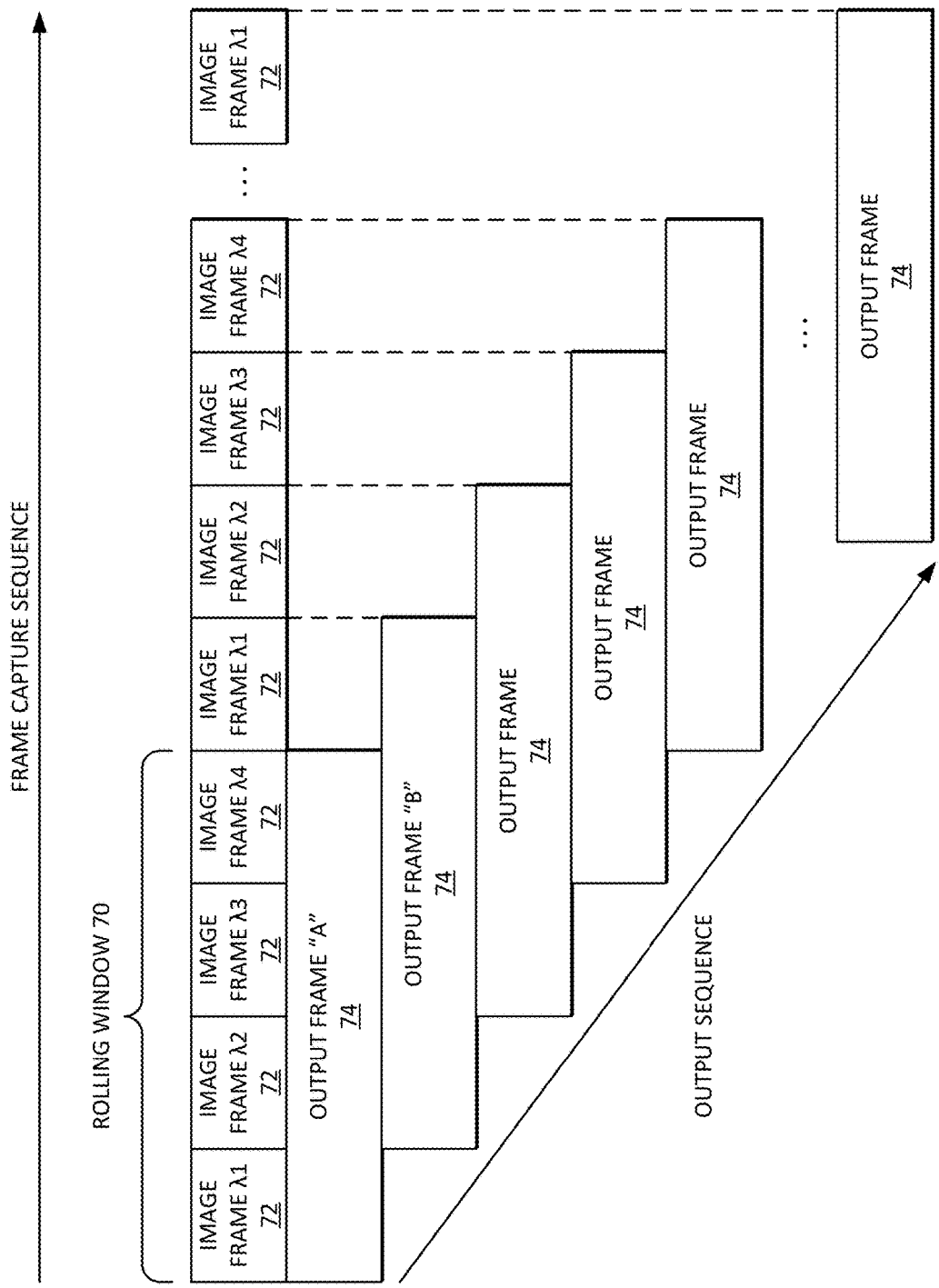
FIG. 3 is a schematic diagram of rolling processing for captured image frames.

The multispectral medical imaging devices and methods discussed herein measure reflectance intensities and compare such to a reflectance standard. Ambient light subtraction and melanin correction are also discussed. Near-video or video frame rates can be achieved in real time. A rolling processing technique and logarithmic difference processing can be used to reduce processing overhead and increase frame rates. Image registration can be used to perform motion correction. Regions of high curvature and regions containing vasculature can be removed or masked from processed oxygen saturation concentration images. A difference mode allows for viewing of oxygen saturation differences over a reference frame. Laser framing and positioning arrays are also provided to assist in proper positioning of the device with respect to the target tissue.

The spectroscopic techniques discussed herein can be used to determine the concentrations of three components of a target tissue, namely, oxygenated hemoglobin, deoxygenated hemoglobin, and melanin. Tissue of interest is illuminated by near-infrared (NIR) light, and some of such light is absorbed by oxygenated hemoglobin, deoxygenated hemoglobin, and melanin, and some light is scattered. Absorption amounts are dependent on wavelength and the concentration of each of the components. Scattering depends on wavelength and path length. Light which is diffusely reflected back is captured by a near-infrared image sensor. The concentration of the three components and the amount of scattered light can be determined by capturing diffusely reflected light from several different wavelength bands of near-infrared light. Measured concentration of melanin can be used to correct concentrations of oxygenated and deoxygenated hemoglobin. Light in the visible spectrum can also be captured and processed. These and many other features and aspects of the invention are discussed below.

FIG. 1 shows a diagram of a multispectral medical imaging device 10 according to an embodiment of the present invention.

The multispectral medical imaging device 10 includes a plurality of illumination devices 12 and 14, an objective lens 16, a beam splitter 18, a near-infrared image sensor 20, and a visible-light image sensor 22.

Near-infrared illumination devices 12 are arranged to illuminate target tissue 24. The near-infrared illumination devices 12 are configured to emit light 26 of different near-infrared wavelength bands. Visible-light illumination devices 14 are arranged to illuminate the target tissue 24 with light 28 in the visible spectrum, such as white light. The near-infrared and visible light emitted 26, 28 by the illumination devices 12, 14 shines on the same general area of the target tissue in a time-sequenced manner, as will be discussed below. The illumination devices 12, 14 may include light-emitting diodes (LEDs) of suitable wavelengths. One or more fly's eye condenser lenses can be provided in the path of the illumination devices 12, 14 to improve uniformity of illumination. In many implementations, the visible-light illumination devices 14 may be omitted.

In this example, the near-infrared illumination devices 12 are four LEDs having near-infrared wavelength bands with nominal peak wavelengths of about 740, 780, 850, and 940 nm.

The objective lens 16 is positioned to capture light 30 reflected from the target tissue 24 and to direct such captured light 30 to the beam splitter 18. The objective lens 16 can be of any suitable type and configuration. Relay optics may also be provided. In one example, the size of the region of the target tissue 24 to be analyzed is about 200 mm by about 150 mm, and the objective lens 16 can be appropriately selected for such area.

The beam splitter 18 can be a dichroic beam splitter, or similar optical device. The beam splitter 18 is arranged to split the captured light 30 received from the objective lens 16 into near-infrared light 32 and visible light 34. The beam splitter 18 is arranged to direct the captured near-infrared light 32 to the near-infrared image sensor 20 and to direct the captured visible light 34 to the visible-light image sensor 22. In one example, the beam splitter 18 directs wavelengths of less than about 700 nm to the visible-light image sensor 22 and directs wavelengths of greater than about 700 nm to the near-infrared image sensor 20.

The near-infrared image sensor 20 is positioned to capture near-infrared light 32 reflected from the target tissue 24 through the objective lens 16. The near-infrared image sensor 20 is configured to capture the near-infrared light 32 as a sequence image frames at a frequency in excess of a suitable video frame rates (e.g., greater than 24 frames per second or FPS). Adjacent frames of different near-infrared wavelength bands are combined into a sequence of oxygen saturation frames at a reduce frame rate, such as a video frame rate (e.g., 24 FPS) to produce a dynamic tissue oxygen saturation map, as will be discussed in detail below. The near-infrared image sensor 20 may include a complementary metal-oxide-semiconductor (CMOS) device with high sensitivity to near-infrared wavelengths.

The visible-light image sensor 22 is positioned to capture visible light 34 reflected from the target tissue 24 through the objective lens 16. Visible-light image frames can be included in the sequence of image frames capturing the near-infrared light 32, and can be captured that the same rate as each near-infrared wavelength band or at a lower rate. The visible-light sensor 22 may include a Bayer-masked RGB CMOS device.

The multispectral medical imaging device 10 further includes an illumination driver 40, an image capture buffer 42, memory 44, a processor 46, a display 48, and a user interface 52.

The illumination driver 40 is connected to the processor 46. The illumination driver 40 is a circuit that controllably provides driving power to the illumination devices 12, 14 and operates the illumination devices 12, 14 according to a sequence controlled by the processor 46.

The image capture buffer 42 includes memory that is connected to the image sensors 20, 22 and is operable to buffer image frames captured by the near-infrared and visible-light image sensors 20, 22. The image capture buffer 42 is connected to the processor 46 to allow the processor 46 to control the capture sequence of the image frames. The image capture buffer 42 is also connected to the memory 44, which provides storage space for captured and/or processed image frames.

The memory 44 is connected to the processor 46 and stores captured and/or processed image frames and one or more programs that are executable by the processor 46 to implement the functionality described herein. The memory 44 provides short-term working memory space for temporary variable and intermediate processed values or images. The memory can also provide long-term storage for indefinite recording of dynamic tissue oxygenation maps and similar. The memory 44 can include any single or combination of devices such as random-access memory (RAM), read-only memory (ROM), flash memory, a hard-disk drive, an optical storage drive, and the like.

The processor 46 may be any kind of microprocessor, central processing unit (CPU), multi-core processor, field-programmable gate array (FPGA), or the like. The processor 46 is configured by one or more programs to modulate near-infrared and visible light 26, 28 output by the plurality of illumination devices 12, 14 to illuminate the target tissue 24. The processor 46 can modulate the illumination devices 12, 14 to illuminate the target tissue 24 by sequentially driving the illumination devices 12, 14 and capturing image frames in a sequence, in which each image frame corresponds to illumination of the target tissue by a different wavelength band. The processor 46 is further configured, by one or more programs, to determine reflectance intensities from image frames captured by the image sensors 20, 22 and to generate a dynamic tissue oxygen saturation map of the target tissue 24 using the reflectance intensities. This will be discussed in further detail below.

The display 48 is an output device that is connected to the processor 46 and configured to display the dynamic tissue oxygen saturation map 50, which may be performed in real time and/or at video frame rates. The display 48 can be positioned for convenient viewing by a clinician or other user operating the device 10. An additional or alternative output device is a projector that projects the dynamic tissue oxygen saturation map onto the target tissue 24, so that the tissue oxygenation map can be viewed as overlaid with the tissue itself.

The user interface 52 is connected to the processor 46 and can include user interface controls such as buttons, switches, dials, touch-sensitive elements of the display 48, a combination of such, or similar. The user interface 52 allows for clinician control of the multispectral medical imaging device 10, including powering on/off, turning on/off various components (e.g., laser framing/focusing), adjusting settings (e.g., thresholds or parameters discussed herein), and making selections such as selecting a reference frame for a temporal difference operation, which will be discussed below.

The multispectral medical imaging device 10 can further include one or both of a laser positioning array 60 and a laser framing array 62. The laser positioning array 60 includes two laser sources 64, such as diode lasers, that are arranged to emit laser beams in the general direction of the target tissue 24. Positioning spots are shined onto the target tissue, and the device 10 can be moved backward or forward, away from or towards the target tissue, to cause the positioning spots to move. The positioning spots are used to indicate whether a correct focus position for the objective lens 16 has been reached or whether the device 10 should be moved toward or away from the target tissue 24 to reach the correct focus position. This will be discussed in further detail below.

The laser framing array 62 includes at least one laser source 66, such as a diode laser, that is arranged to emit at least one beam toward the target tissue 24. One or more laser points are shined onto the target tissue, and the device 10 can be rotated, titled, or otherwise move to align the spots on the target tissue 24. This can assist in repeatedly positioning the target tissue 24 with respect to the objective lens 16 at a desired measurement location during subsequent oxygenation measurement sessions. This will be discussed in further detail below.

The multispectral medical imaging device 10 may further include an ambient-light sensor 68 positioned to detect levels of or changes in background illumination. The ambient-light sensor 68 is connected to the processor 46 and may be a visible-light sensor, an infrared light sensor, a combination of such, or similar.

All or some of the components of the multispectral medical imaging device 10 can be provided in a housing 58, as shown in FIG. 2. Particularly, the housing 58 can contain an opening for the objective lens 16, and all or some of the illumination devices 12, 14 can be arranged in one or more circular rings around the objective lens 16 to promote spatially uniform illumination.

With reference to FIG. 3, the processor 46 is configured to perform rolling processing on a window 70 of image frames 72 corresponding to illumination of the target tissue 24 by each of the near-infrared illumination devices 12. Each image frame 72 corresponds to one of the wavelength bands of the near-infrared illumination devices 12. That is, when the rolling window 70 is at the position illustrated, sequential image frames 72 for wavelength bands λ1, λ2, λ3, λ4 are combined to form an output frame 74 (show as "A"), which is illustrated as wider merely to show the corresponding source image frames 72. When the next image frame 72 (λ1 wavelength band) is captured, the rolling window 70 is moved such that sequential image frames 72 for wavelength bands λ2, λ3, λ4, λ1 are combined to form a subsequent output frame 74 (show as "B"). This process continues for the capture sequence, where the sequence of output frames forms the dynamic tissue oxygen saturation map.

As can be seen, the frame rate of the dynamic tissue oxygen saturation map is approximately equal to a combined frequency of modulation of all wavelength bands outputted by the near-infrared illumination devices 12. That is, a new output frame 74 can be generated after each new near-infrared image frame 72 is captured by the near-infrared image sensor 20. The output frame rate thus decoupled from the number of different near-infrared frequency bands to be sequentially captured. However, this does not take into account capture of visible-light image frames by the visible-light image sensor 22. This also does not take into account ambient near-infrared image frames captured by the near-infrared image sensor 20 when the near-infrared illumination devices 12 are off. Visible-light image frames and ambient near-infrared image frames are captured in sequence with the near-infrared image frame 72, although not necessarily at the same frequency. Increasing the number of visible-light image frames and/or ambient near-infrared image frames captured can reduce overall output frame rate. However this can be beneficial, as such image frames are used for correction purposes.

Figure 4:
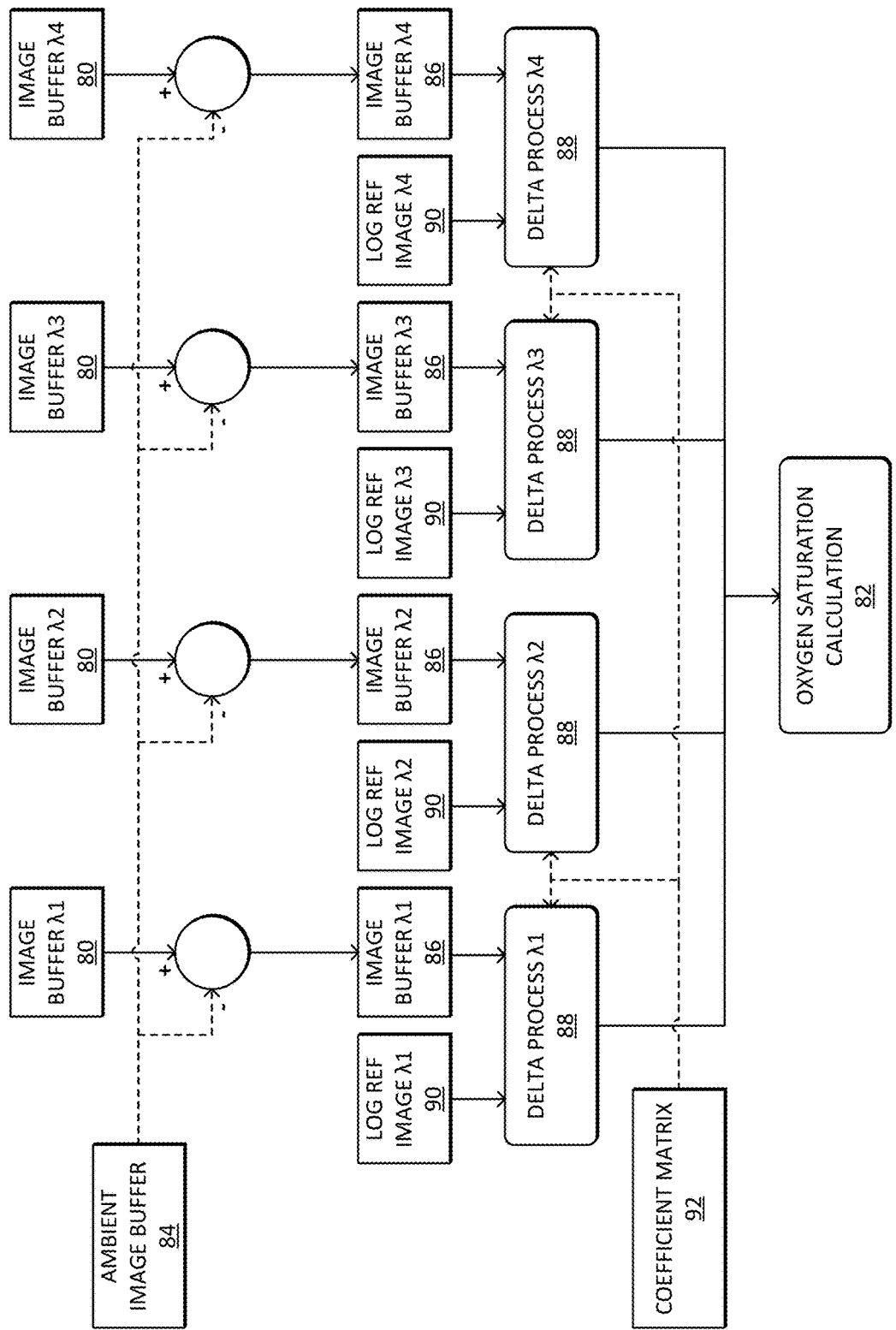
FIG. 4 is a functional block diagram of an oxygen saturation computation performed on captured image frames.

FIG. 4 shows an oxygen saturation computation.

Tissue oxygen saturation is derived from a spectroscopic technique based on the Beer-Lambert Law that utilizes the spatially resolved reflectance of the target tissue at four different near-infrared wavebands to determine the relative concentrations (C) of oxygenated hemoglobin ($HbO_2$) and deoxygenated hemoglobin (Hb). Tissue oxygen saturation can be calculated by the processor 46 according to the following formula:

$$S_T O_2 = \frac{C_{HBO_2}}{C_{HBO_2} + C_{Hb}}$$

The image capture buffer 42 (FIG. 1) can include one or more image buffers 80 for each of the near-infrared wavelength bands λ1, λ2, λ3, λ4 to capture. The image buffers 80 are filled in sequence, as discussed above with respect to the rolling processing. After a next image buffer 80 is filled, the oxygen saturation calculation 82 is performed to obtain tissue oxygen saturation, $S_T O_2$. That is, after the image buffer 80 for wavelength band λ1 is filled with a new near-infrared image frame captured by the near-infrared image sensor 20, the oxygen saturation calculation 82 is performed. Then, after the image buffer 80 for wavelength band λ2 is filled with a new near-infrared image frame captured by the near-infrared image sensor 20, the oxygen saturation calculation 82 is performed again. The cyclic filling of the image buffers 80 repeats, with a new oxygen saturation calculation 82 being performed after each fill.

Prior to the oxygen saturation calculation 82, correction for background or ambient infrared radiation can be performed. A captured ambient image of the target tissue 24 that is stored in an ambient image buffer 84 can be subtracted from each of the contents of the image buffers 80. The results are then forwarded to ambient-corrected image buffers 86.

The ambient image of the target tissue 24 can be captured by the processor 46 switching off the near-infrared illumination devices 12 and controlling the near-infrared image sensor 20 to capture an image frame. This can be performed repeatedly, such as once for each captured sequence of near infrared wavelength bands of interest (e.g., λ1, λ2, λ3, λ4), with the most recent ambient infrared image being kept in the ambient image buffer 84. Alternatively, this can be performed less frequently, such as once for every N captured sequences of near infrared wavelength bands. Suitable values of N can be determined based on expected usage scenarios. For example, it may be sufficient to capture an ambient image frame once each second (e.g., at 24 FPS, N=24). In another example, it may be may be sufficient to capture an ambient image frame once each minute or even at longer intervals. In addition, the processor 46 and ambient image buffer 84 can be configured to calculate and store a time-average of two or more captured ambient images.

Alternatively, the ambient-light sensor 68 connected to the processor 46 can be used to trigger capture of an ambient image when the processor 46 determines that there has been a change in ambient infrared illumination that exceeds a threshold. The ambient-light sensor 68 can be an infrared light sensor capable of detecting the change directly. Alternatively, the ambient-light sensor 68 can be a visible-light sensor that detects a change in ambient visible illumination that may be indicative of the change in ambient infrared illumination.

Delta or change-based processing 88 is performed on images stored in the ambient-corrected image buffers 86. For each wavelength band, the delta processing 88 uses logarithmic values of a reference image 90 that acts as a reference standard for the particular wavelength band. The delta processing 88 further references a coefficient matrix 92 that relates reflectance intensities to concentrations of oxygenated and deoxygenated hemoglobin. This can reduce processing overhead and increase output frame rate.

The logarithmic values of the reference image 90 can be pre-calculated based on captured near-infrared images of about 100% diffuse reflectance, and these can be established during an initial calibration process, which may be performed at time of manufacture.

Figure 5:
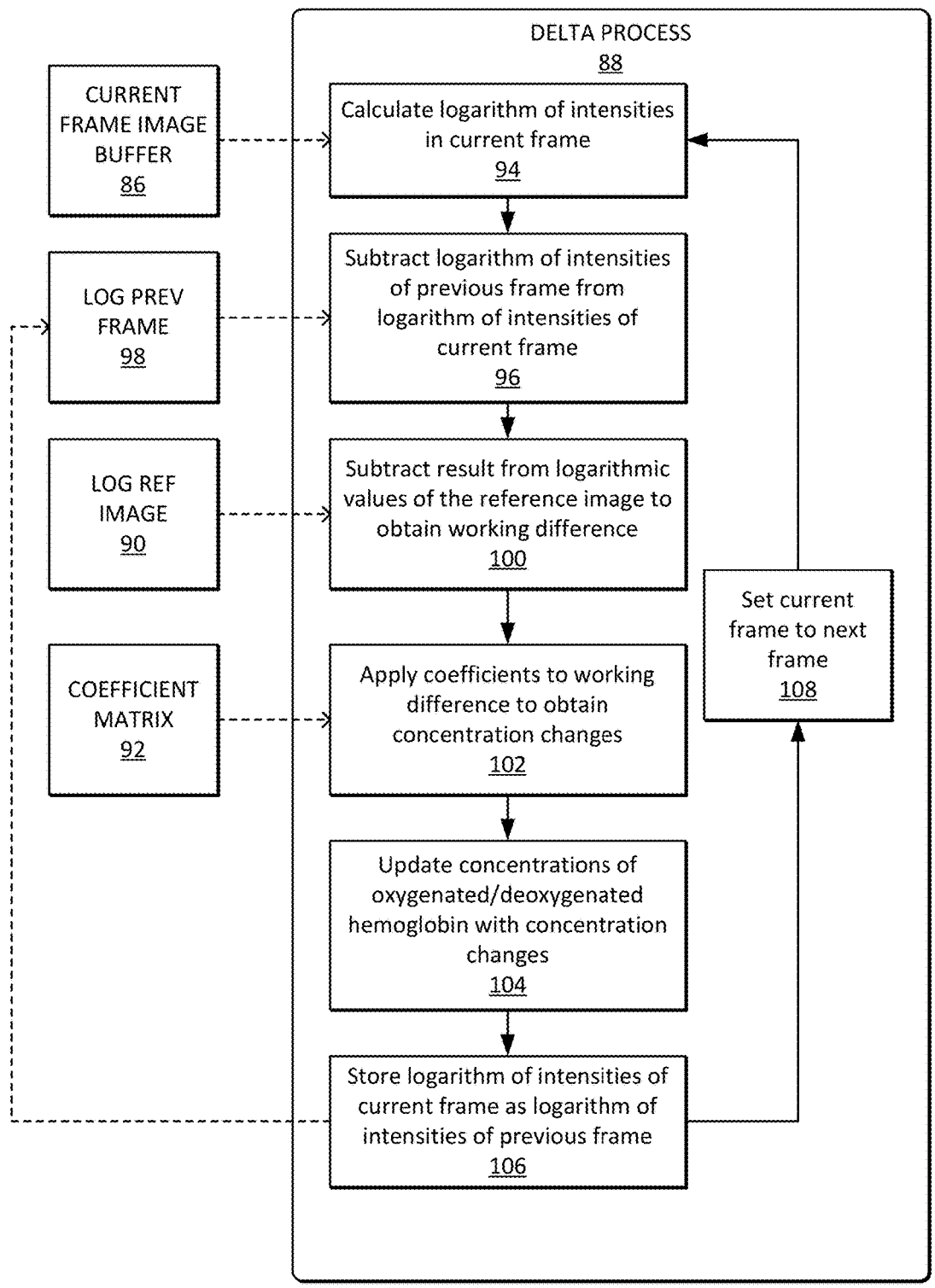
FIG. 5 is a diagram of a delta process used for the oxygen saturation computation.
Figure 6:
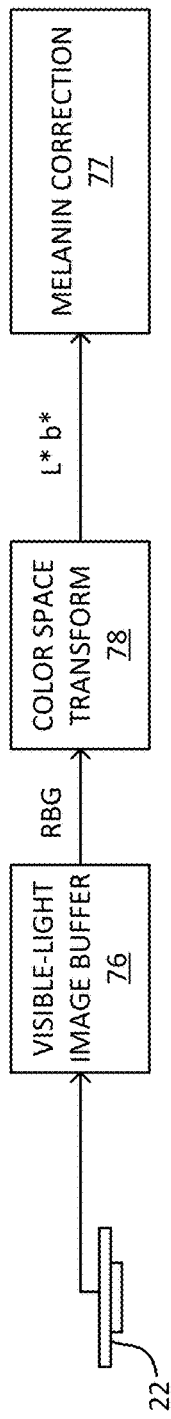
FIG. 6 is a diagram of a melanin correction operation.

The delta processing 88 is shown in detail in FIG. 5. Images for each near-infrared wavelength band undergo the same general processing 88, as executed by the processor 46.

At step 94, a logarithm function is applied to reflectance intensities or values for the current image frame. Then, at step 96, stored logarithm values of the previous frame 98 are subtracted from the calculated logarithm values of the current frame obtained in step 94. Next, at step 100, the result of step 96 is subtracted from the logarithmic values of the reference image 90 to obtain a working difference (i.e., temporary values). Coefficients 92 are applied to the working difference to obtain concentration changes, at step 102. Step 104 includes updating previous values of concentrations of oxygenated and deoxygenated hemoglobin with the concentration changes from step 102 to reflect the change in the intensity of diffuse reflectance for the wavelength band. At step 106, the logarithm values for the current frame are stored as the logarithm values of the previous frame 98. The process then advances to the next frame at step 108.

The delta processing 88 can be implemented by one or more functions, procedures, formulas, algorithms, a combination of such, or similar. The steps are illustrative and may be performed in a different order or combined into larger steps. The logarithm function can be implemented as a lookup table stored in memory 44.

An example for the coefficient matrix 92 is shown in the below formula. The left-hand side of the equation represents intensity of light captured by the near-infrared image sensor 20 for the various wavelengths. $A\lambda 1$-$A\lambda 4$ is representative of the diffuse reflectance. The right-hand side has two parts: a constant part and a variable part. The constant part contains terms representative of the coefficient of absorption, $\epsilon$, for the various near-infrared wavelengths of interest for both oxygenated hemoglobin ($HbO_2$) and deoxygenated hemoglobin (Hb). The constant part can be pre-computed and stored in the coefficient matrix 92. The variable part contains concentrations, C, of oxygenated hemoglobin ($HbO_2$) and deoxygenated hemoglobin (Hb) that are the sought values, modified by a factor, L, representative of the thickness of the layer melanin distribution.

$$\begin{bmatrix} A\lambda_1 \\ A\lambda_2 \\ A\lambda_3 \\ A\lambda_4 \end{bmatrix} = \begin{bmatrix} \ln(10)\varepsilon_{HbO2}(\lambda_1) & \ln(10)\varepsilon_{Hb}(\lambda_1) \\ \ln(10)\varepsilon_{HbO2}(\lambda_2) & \ln(10)\varepsilon_{Hb}(\lambda_2) \\ \ln(10)\varepsilon_{HbO2}(\lambda_3) & \ln(10)\varepsilon_{Hb}(\lambda_3) \\ \ln(10)\varepsilon_{HbO2}(\lambda_4) & \ln(10)\varepsilon_{Hb}(\lambda_4) \end{bmatrix} \begin{bmatrix} C_{HbO2}L \\ C_{Hb}L \end{bmatrix}$$

The processor 46 can be configured to perform melanin correction 77 for the skin over the target tissue 24. This can be performed using a Beer-Lambert model using melanin (M), deoxygenated hemoglobin (Hb), and oxygenated hemoglobin ($HbO_2$) as chromophores.

Measured diffuse reflectance for the each wavelength of interest, $A\lambda 1$-$A\lambda 4$, can be modelled according to the following equation, in which $R_S$ represents the as-measured intensity of light at a particular wavelength, $R_O$ represents the reference image intensity for the wavelength, $\epsilon_M$ represents the coefficient of absorption for melanin, and $C_M$ is the concentration of melanin in the target tissue.

$$A\lambda = -\ln(R_S(\lambda)/R_O(\lambda) - \epsilon_M(\lambda)C_M L$$

The effect of melanin reduces the as-measured intensity of light. Melanin concentration $C_M$ and thickness L are combined into a single parameter $Z_{mel}$. Determining the concentration of melanin is performed using the visible-light image sensor 22 and a pre-calculated calibration curve for $Z_{mel}$.

Output of the visible-light image sensor 22 can be stored in a visible-light image buffer 76 of the overall image buffer 42 (FIG. 1). In this example, the melanin correction is performed in the CIELAB color space. If the visible-light image sensor 22 is selected to be a RBG sensor, then the processor 46 is configured to perform a color space transformation 78 to obtain L*a*b* values from captured RBG values.

The processor 46 is configured to obtain a specific value of the correction parameter $Z_{mel}$ using lightness, L*, and color-opponent dimension, b*, values. The L* and b* values can relate to a characteristic angle, $\alpha$, by an empirical formula, such as:

$$\alpha = \tan^{-1}\left(\frac{L^* - 50}{b^*}\right)$$

Figure 7:
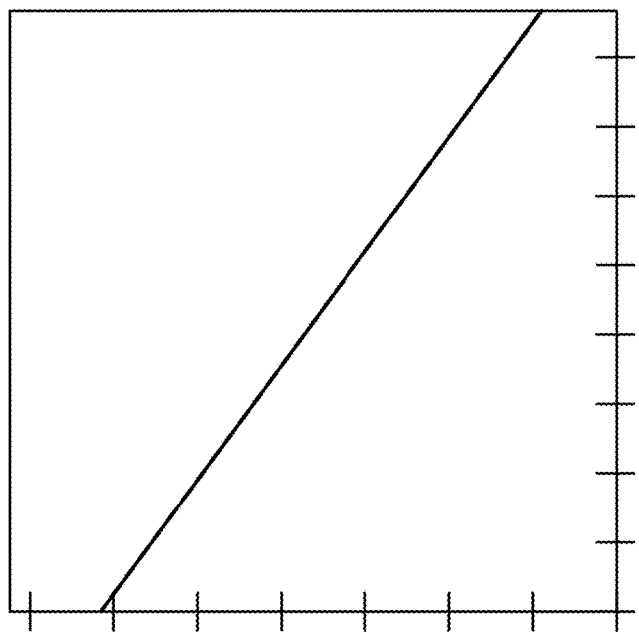
FIG. 7 is a chart of a melanin correction parameter.

The characteristic angle, $\alpha$, is then applied to a pre-calculated calibration curve, as shown in FIG. 7, to obtain the specific value of the correction parameter $Z_{mel}$ for the skin above the target tissue 24. The calibration curve can be empirically determined using a reference device and a variety of different skin tones. The calibration curve can be stored in memory 44.

Once the value of the melanin correction parameter $Z_{mel}$ is obtained and the intensity, $R_S$, of near-infrared light of the wavelengths of interest have been measured, the above equations reduce to two equations for tissue oxygen saturation, $S_TO_2$, of the form:

$$S_TO_2 = \frac{L \cdot C_{HbO_2}}{L \cdot C_{HbO_2} + L \cdot C_{Hb}}$$

in which tissue oxygen saturations, $S_TO_2$, are known and two unknowns remain, being the deoxygenated hemoglobin (Hb) and oxygenated hemoglobin ($HbO_2$) concentrations (layer thickness factor, L, canceling). Solving these two equations and two unknowns forms the oxygen saturation calculation 82 (FIG. 4).

The above equations and/or calculations can be stored in memory 44 (FIG. 1) as a predetermined relationship between visible light intensity and melanin concentration.

Figure 8:
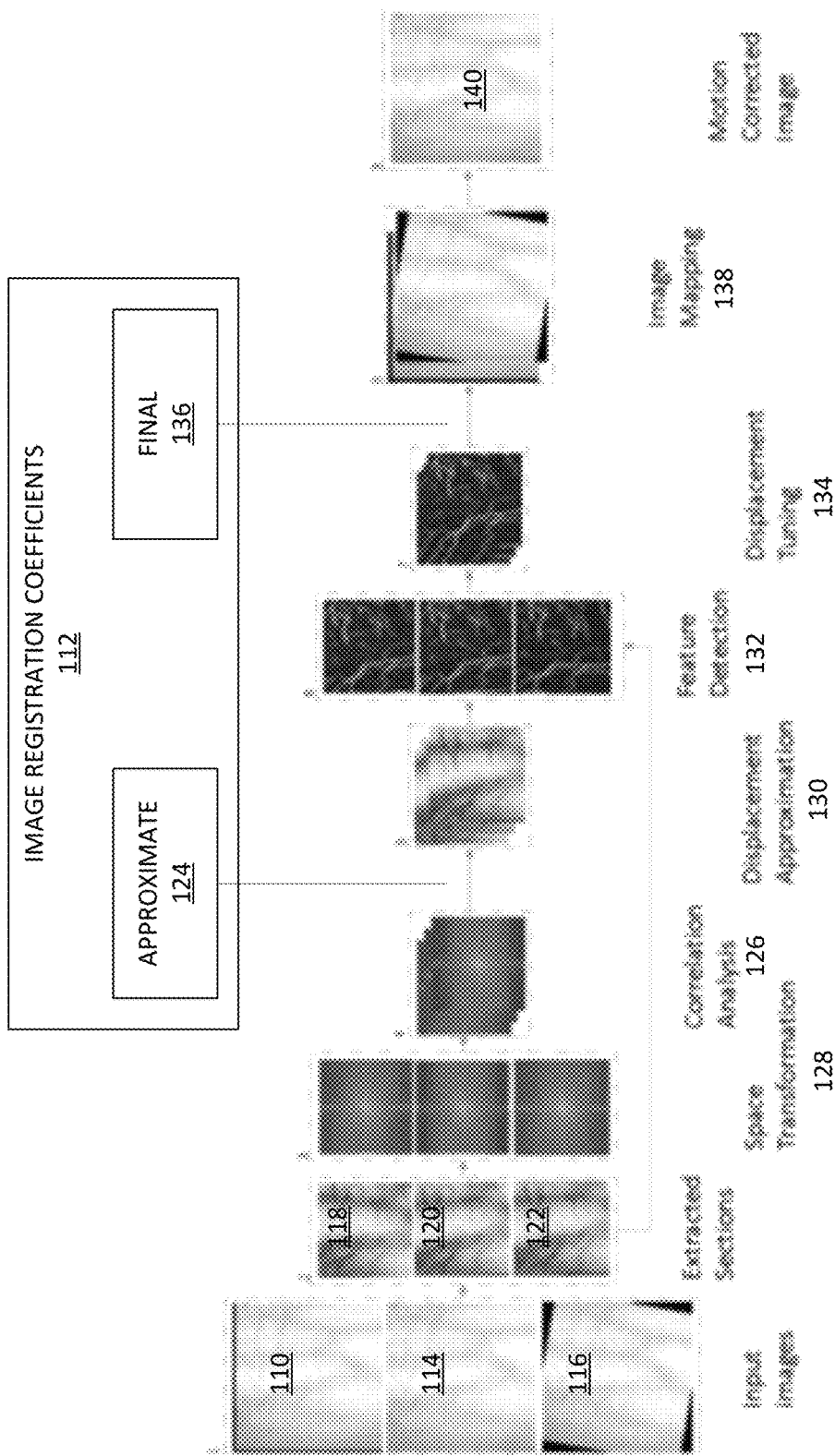
FIG. 8 is a diagram showing a motion correction process.

With reference to FIG. 8, the processor 46 can be configured to perform motion correction on image frames captured by the near-infrared image sensor 20.

Motion correction is performed using the image registration technique to determine a geometrical transformation that aligns points in at least one image frame of the target tissue 24 with corresponding points in another image frame of the target tissue 24.

Motion correction can include selection of a reference frame 110 and calculating image registration coefficients 112 for at least one subsequent frame 114, 116 of the captured image frames. Referring back to FIG. 4, captured image buffers 80 or ambient-corrected image buffers 86 may be used to store temporally successive image frames for each wavelength band. That is, each image buffer 80 can be configured to store two or more temporally contiguous image frames, or each image buffer 86 can be configured to store such. In the example discussed herein, three successive image near-infrared frames are used for motion correction. Motion correction can equally be performed on successive visible-light image frames in the same manner.

Due to motion of the target tissue 24 with respect to the multispectral medical imaging device 10, the actual position and rotation of the subsequent frames 114, 116 may be different from those of the reference frame 110.

The reference frame 110 may be the first image frame captured in a particular clinical session of the multispectral medical imaging device 10. That is, the same reference frame 110 may be used for the entire duration of a patient's imaging session (e.g., a few minutes). In such case, the processor 46 can be configured determine excessive motion correction based on particular threshold values of the calculated image registration coefficients and issue a warning to the clinician. Alternatively or additionally, a new reference frame 110 may be periodically selected, such as every few seconds, every M image frames (M=10, 40, or 100, etc.), or similar, to reduce the likelihood that the image registration coefficients will demand too much motion correction or become too inaccurate.

Sub-regions 118, 120, 122 of the respective image frames 110, 114, 116 may be extracted and calculation of image registration coefficients 112 may be performed on the sub-regions 118, 120, 122, as opposed to the entire image frame 110, 114, 116. The sub-regions 118 have dimensions smaller than a size of the image frames 110, 114, 116 and are located away from edges of the image frames. In this example, each sub-region 118, 120, 122 is the central portion of the respective image frames 110, 114, 116. Any suitable size may be used for the sub-regions. For instance, if each image frame 110, 114, 116 is 640 by 480 pixels, then each sub-regions 118, 120, 122 may be a centrally located region of 320 by 240 pixels.

Use of sub-regions 118, 120, 122 may be beneficial, as no significant image background is expected to be present in the image frames. That is, no objects are expected to move with respect to a stationary background. Rather, the entire view itself may move due to movement of the patient or the device 10. Accordingly, new information may enter the field of view and existing information may leave the field of view. The sub-regions 118, 120, 122 convey features that remain common during movement, and thus permit motion correction. Moreover, given that the sub-regions are smaller, the overall image registration process can be made faster.

Approximate values 124 of the image registration coefficients 112 are determined by the processor 46 performing a correlation analysis 126 on space transformation 128 of the sub-regions 118, 120, 122 of the image frames 110, 114, 116, which provides for displacement approximation 130 for the subsequent frames 114, 116.

After determination of the approximate values 124 of the image registration coefficients 112, the processor 46 uses the approximate values 124 to apply displacement and rotation approximations to the sub-regions 120, 122 of the subsequent image frames 114, 116. This coarsely aligns the sub-regions 120, 122 with the reference sub-region 118. The processor 46 then performs feature detection 132 on the approximately aligned sub-regions 118, 120, 122 of the image frames 110, 114, 116, so as to fine tune 134 the approximate displacements and calculate final values 136 for the registration coefficients 112.

Discrete determination of approximate values 124 of the image registration coefficients 112 final values 136 for the registration coefficients 112 can increase speed of image registration as well as reduce processing demand, in that feature detection is performed on images that are coarsely aligned.

With regard to near-infrared image frames captured by the near-infrared image sensor 20, feature detection 132 can include detection of vasculature of the target tissue 24. Vasculature may exhibit edges and strong features that can assist calculation of the final values 136 for the image registration coefficients 112.

With regard to image frames captured by the visible-light image sensor 22, body hair on skin over the target tissue 24. Body hair, which is often an unwanted feature in vasculature imaging, can be specifically targeted by the feature detection 132 as body hair has been found to provide strong edges. Additionally or alternatively, feature detection can include detection of an ink mark on a skin surface over the target tissue 24. Such a mark can be placed by a clinician.

The processor 46 then performs image mapping 138 to use the final values 136 for the image registration coefficients 112 to align the subsequent image frames 114, 116 with the reference image frame 110 to arrive at one or more motion corrected images 140.

The motion correction process shown in FIG. 8 can be performed for each wavelength band captured, including one or more near-infrared wavelength bands and visible wavelength bands. Accuracy of image registration, and thus accuracy of motion correction, can be increased when such is performed on at least one near-infrared band and a visible band, given that each of these wavelength bands offers distinct features.

The image registration techniques discussed above for motion correction can also be used to automatically align image frames captured by the two image sensors 20, 22 to correct for misalignment of the two image sensors 20, 22 with respect to each other. Misalignment can be considered a motion artifact that is correctable via a process similar or identical to the above-discussed motion correction process. To achieve misalignment correction, one or more images of a standard pattern are captured by the two image sensors 20, 22. The standard pattern images are subsequently used by the image registration process to derive displacement coefficients. This procedure can be performed once, at manufacture, to determine displacement coefficients that can be stored in memory 44 for the service life of the device 10. During operation, the processor 46 references the displacement coefficients to align captured images from the two image sensors 20, 22 with one another. This can advantageously permit some error in physical alignment of the two image sensors 20, 22 during manufacture, while providing for digital alignment between near-infrared and visible-light images so as to improve the melanin correction and any other corrections that reference visible-light images.

Figure 9:
FIG. 9 is an example output image showing example oxygen saturation concentrations and a curvature mask.

As shown in FIG. 9, the processor 46 can also be configured to perform masking to omit regions of high curvature from the dynamic tissue oxygen saturation map 50. FIG. 9 shows a sample image of the dynamic tissue oxygen saturation map 50 of the target tissue. A large central region 150 contains, in false color, oxygenation/deoxygenating information, as determined using the techniques discussed herein. Regions of high curvature, with respect to the plane of the map 50, are masked to replace oxygenation/deoxygenating information with visualization selected to enhance clinician understanding. An example of a mask over a high curvature region is shown at 152.

Radiant intensity observed from a diffusely reflecting surface, such as the target tissue 24, is directly proportional to the cosine of the angle between the line of sight of the objective lens 16 (FIG. 1) and the surface normal. Any curvature of the target tissue can reduce the intensity of the light being captured by the image sensors 20, 22. Error in the oxygen saturation value caused by surface curvature may mislead the clinician. The mask is selected to be applied to areas where the error is greater than a threshold amount.

To generate the mask 152, captured image frames of each of the near infrared wavelength bands are analyzed to identify regions where the radiant intensity has fallen by more than the threshold amount with respect to an adjacent region. In one example, the threshold amount of change in intensity can be selected to be 20%. This can be performed on a pixel-by-pixel basis. The mask is applied to regions common to all captured near-infrared image frames 72 (FIG. 2) contributing to the same output frame 74 where the processor 46 determines that intensity has fallen by more than the threshold amount. This can indicate the presence of a threshold amount of curvature for the target tissue in the region considered.

Figure 10:
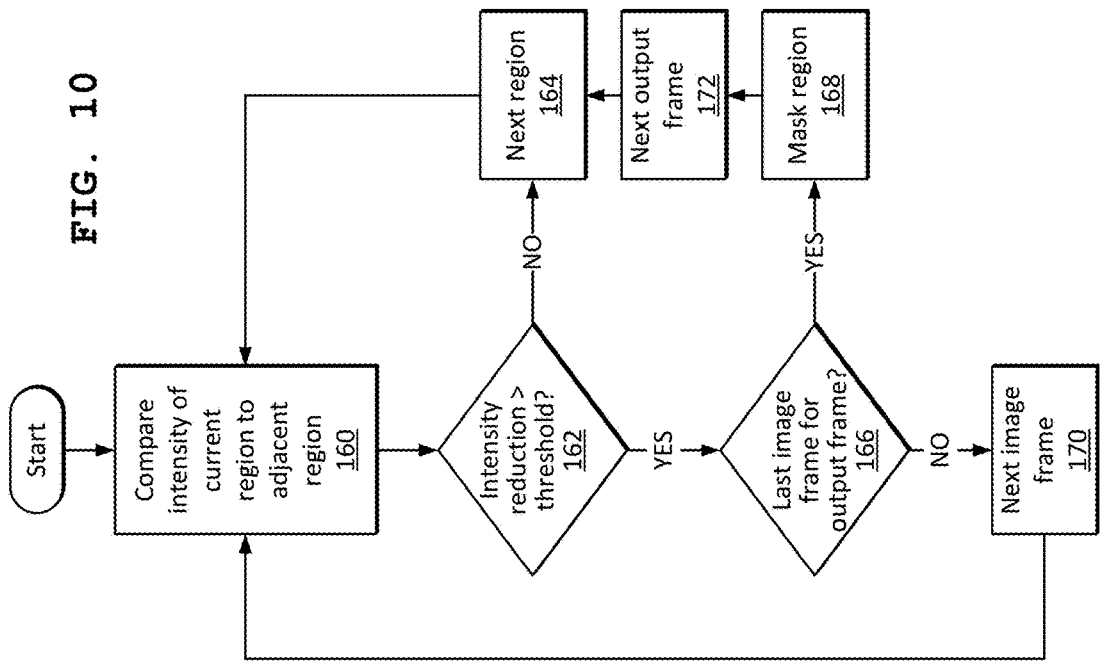
FIG. 10 is a flowchart of a process for determining a curvature mask.

The flowchart of FIG. 10, illustrates an example of the masking process. This is merely an example, and in implementation other processes, algorithms, or calculations may be used.

At step 160, a current region of a current near-infrared image frame contributing to a current output image is analyzed. The intensity value of the current region is compared to that of one or more adjacent regions. Each region can be a pixel or a group of pixels. If the intensity value of the current region is not lower than the intensity value of the adjacent region by at least the threshold amount, at step 162, then no masking is performed for this region and the next region in the current image is selected, at step 164. If the intensity value of the current region is lower than the intensity value of the adjacent region by at least the threshold amount and the current image frame 72 (FIG. 2) is the final image frame 72 analysed for a set of image frames belonging to an output frame 74, as determined by step 166, then the test of step 162 has been met for all image frames 72 contributing to the current output frame 74 and the region is masked, at step 168. Otherwise, step 166 determines that there are other image frames to analyze for the current output frame, and step 170 select the next of such image frames. After a region is determined to be masked, at step 168, then the process advances to the next output frame, at step 172 and a first region is selected for a first image frame of such output frame, at step 164.

Alternatively or additionally to masking, if the curvature of the target tissue 24 is known or can be estimated or calculated, then one or more curvature correction factors can be applied to compensate for the effect of curvature.

As also shown in FIG. 9, the processor 46 can further configured to use the near-infrared image frames to identify veins in the target tissue 24 and to omit the veins from the dynamic tissue oxygen saturation map 50. Measured reflectance intensities can be modified to compensate for the effect of oxygenation/deoxygenating at the veins, so as to effectively hide the veins from view and thus omit information not relevant to visualization of tissue oxygenation. Analysis of reflectance intensities of near-infrared image frames to detect veins can include analyzing either side of the isosbestic point.

The feature extraction techniques previously described with respect to motion correction can be implemented to achieve vein compensation. The processor 46 can be configured to execute feature extraction to detect vein boundaries and interiors and to enhance vein regions for visualization. The processor 46 can be configured to modify the dynamic tissue oxygenation map with one or more masks determined from detected vein regions. Additionally or alternatively, the device 10 can be configured to output, via the display 48, an indication of vein contribution to the dynamic tissue oxygenation map. Such indication may include vein outlines, or similar visualization.

Figure 11:
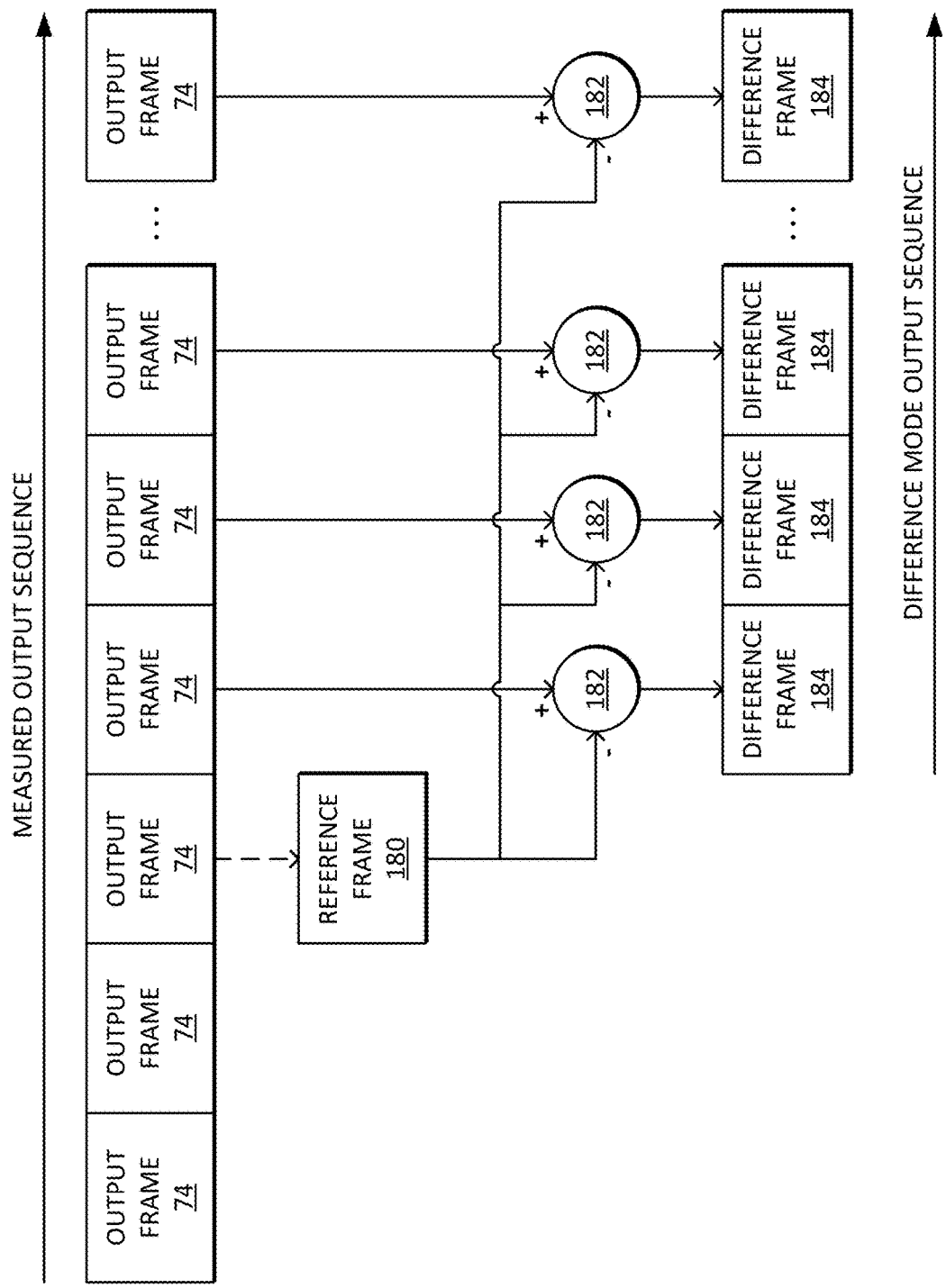
FIG. 11 is a diagram showing a process for generating a dynamic difference map for oxygen saturation.

As shown in FIG. 11, the processor 46 can further be configured to perform a temporal difference operation on a sequence of frames of the dynamic tissue oxygen saturation map. The temporal difference operation shows oxygen saturation with respect to a reference frame of the dynamic tissue oxygen saturation map.

A sequence of output frames 74, as measured using the techniques discussed herein, can be output in real time or played back from memory. The output frames 74 form dynamic tissue oxygen saturation map of the target tissue. One of such output frames 74 can be selected as a reference frame. A difference operation 182 can be used to subtract the reference frame 180 from subsequent output frames 74 to obtain difference frames 184. The difference operation 182 can be a simple difference or a higher-order difference. The difference frames 184 can be output in real time or played back from memory as a dynamic tissue oxygen saturation difference map. When the dynamic tissue oxygen saturation map is being recorded, different frames 184 can also be calculated as above for output frames 74 that are earlier than the reference frame 180.

The specific reference frame 180 can be selected by the clinician, so as to observe and record changes in oxygen saturation relative to the reference without the need for a contrast agent. Such can facilitate analysis of the limits of perfusion of a perforator. For instance, the clinician first clamps/blocks the perforator of interest and waits for specified duration of time (e.g., 2 minutes) before setting the current output frame 74 as the reference frame 180. Then, the clinician releases/opens the clamped/blocked perforator. The difference map (before release and after release) can be used to quantify the area of the tissue being supplied by the perforator and also identify the limits of perfusion of the perforator. Moreover, by repeating the limits of perfusion test on each of a set of perforators and using the dynamic tissue oxygen saturation map to quantify the area supplied by each perforator, the clinician can identify the dominant perforator.

An example of the laser framing array 62 is shown in FIG. 12. Each of the lasers 66 is positioned to emit its laser point 190 onto the skin surface over the target tissue. The laser points are for assisting manual positioning of the device 10 with respect to the target tissue. The laser sources 66 can be arranged to provide points 190 in any suitable arrangement, such as the rectangle shown. The region defined by the points can be considered a region of interest 192 for multispectral imaging of tissue oxygenation. Any number of two or more laser sources 66 may be used.

The laser sources 30 may be selected to have any suitable wavelength. If visible-light lasers are used, the visible-light image sensor 22 can capture light from the laser points reflected from the skin surface. The processor 46 can be further configured to include the laser points 190 in the dynamic tissue oxygen saturation map by extracting the points 190 from visible-light image frames and inserting the points 190 or representations thereof into output image frames. Visible-light lasers have the advantage of not interfering with near-infrared image processing and will not significantly affect the oxygenation map. If near-infrared lasers are used, a suitable near-infrared wavelength can be selected so that the near-infrared image sensor 20 inherently captures the points 190 as part of the image capture process. The laser points 190 are then including in the dynamic tissue oxygen saturation map without additional processing. However, it may be desirable to further configure the processor 46 to detect and ignore the laser points 190 when performing oxygenation calculations.

It may be clinically useful to be able to compare images from different points in time for the same anatomical region of the patient. These images may be taken at different points in a single procedure, minutes or hours apart, or may be taken days or even weeks apart, as part of a procedural pre-assessment for procedural planning, or post-assessment to monitor or evaluate progress Images taken during different sessions should be matched so that they are comparing the same anatomical region at the same scale and rotation. The laser framing array 62 can serve to visually assist the user of the device 10 in positioning the objective lens 16 normal to the surface being imaged. In the example above, it would be expected for the points 190 to form a rectangular shape around the region of interest 192. Any skewing (e.g., the points defining a keystone or trapezoidal shape) would indicate to the clinician that the target tissue or the device 10 may need to be repositioned.

With reference to FIG. 13, the laser points 190 can be recorded to a captured image. Hence, recorded laser points 194 in a previously recorded image 196 can form an easily identified visual reference between the objective lens's view of the target and presently projected laser points 190. Thus, a clinician capturing a new image can manually align both anatomical features 198 (i.e., veins, hair, navel, margins) between the previously recorded image 196 and such features 200 in the new image, as well as the laser points 190 in the new image as compared to the laser points 194 in the recorded image 196. Manual alignment can include translating/rotating one or both of the target and the device.

As also shown in FIG. 13, the laser sources 66 may be mounted to the housing 58 of the device 10 in the vicinity of the objective lens and generally aimed in the same direction as the principal optical axis of the objective lens.

If there is apparently accurate alignment between anatomical features 200, 198 in the recorded and new images, but there is a difference between the positions of the laser points 190, 194, then the processor 46 can apply a spatial transform, such as a bilinear transform, to correct the spatial difference between the two images. This can be used to correct for fine differences in normality/skew between the two images.

Accurate alignment between stored and new images may allow for accurate comparison of precise localized changes in tissue oxygenation. This can allow clinicians to improve care and/or initiate interventions.

FIG. 14 illustrates another laser framing array 204 suitable for use as the laser framing array 62. Line generating optics 206 may be provided to emit lines 208 of laser light onto the skin surface over the target tissue. The lines 208 of laser light include the laser points 190 previously discussed, and the same general principles apply. The above description may be referenced. The lasers 66 and optics 206 may be arranged so that the lines form a rectangular box or other shape that bounds the region of interest 192. One advantage of laser lines is that operators may find them more visible, and therefore the device 10 may be more convenient to use.

FIG. 15 shows an example of the laser positioning array 60 configured to assist in positioning the device 10 at a target distance from the target tissue, the target distance being, for instance, a suitable focal distance of the objective lens. An example target distance is about 610 mm.

A first positioning laser 64 is positioned at a first offset distance from the optical axis 210 of the objective lens 16 and is aimed at a first angle 212 with respect to the optical axis 210. The first positioning laser 64 is aimed to emit, as shown in FIG. 16A, a first positioning laser spot 214 on a skin surface 216 over the target tissue. The first positioning laser 64 is affixed to the housing 58 or other component of the multispectral medical imaging device 10. Hence, as the device 10 is moved towards and away from the surface 216, the first positioning laser spot 214 traverses along a first path 218.

A second positioning laser 64 is positioned at a second offset distance from the optical axis 210 of the objective lens 16 and is aimed at a second angle 220 with respect to the optical axis 210. The second positioning laser 64 is aimed to emit, as shown in FIG. 16A, a second positioning laser spot 222 on a skin surface 216. The second positioning laser 64 is affixed to the housing 58 or other component of the device 10. Hence, as the device 10 is moved towards and away from the surface 216, the second positioning laser spot 222 traverses along a second path 224.

The first and second angles 212, 220 lay in different planes that each contains the optical axis 210. The optical axis 210 can be considered the intersection of these planes. That is, the first and second positioning lasers 64 are each laterally offset from the optical axis 210 and are also angularly offset from each other. If the first positioning laser 64 is at a position of 0 degrees on a circle centered at the optical axis, the second positioning laser 64 is at a different angle, such as 90 degrees. In this example, the first and second positioning lasers 64 are positioned at about 90 degrees apart.

The first and second offset distances and the first and second angles 212, 220 are selected to cause the first positioning laser spot 214 and the second positioning laser spot 222 to be coincident at the optical axis when the target tissue is a target distance from the objective lens 16. This is shown in FIG. 16C.

The first and second offset distances and the first and second angles 212, 220 can be selected to position the first and second positioning laser spots 214, 222 on one side 230 of the optical axis 210 of the objective lens 16 when a distance from the objective lens to the surface 216 of the target tissue is greater than the target distance (FIG. 16A). Conversely, when the distance from the objective lens to the target tissue is less than the target distance, the first and second positioning laser spots 214, 222 appear on an opposite side 232 (FIG. 16B).

As the clinician moves the device 10 relative to the target tissue, or vice versa, the two positioning spots 214, 222 move along their respective paths 218, 224. The positioning spots 214, 222 appear as separate spots on one side 232 of the target surface 216 if the device 10 and target tissue are too close, as shown in FIG. 16B. The positioning spots 214, 222 appear as separate spots on an opposite side 230 of the target surface 216 if the device 10 and target tissue are too far, as shown in FIG. 16A. Adjusting the distance of the device 10 to the target tissue in a direction that causes the spots to diverge indicates to the clinician that the adjustment is opposite to what is required. Adjusting the distance of the device 10 to the target tissue in a direction that causes the spots 214, 222 to converge indicates to the clinician that the adjustment is in the correct direction, until the spots 214, 222 become coincident thereby indicating that the target distance has been reached, as shown in FIG. 16C.

The visible-light image sensor 22 and the processor 46 can be configured to capture and monitor the positions of spots 214, 222 and output, via the display 48 or an component of the user interface 52, such as a speaker, an indication to the user as to the positions of the spots 214, 222 and/or the direction in which to move the device 10 to arrive at the target distance. Such indications can be of the form of raw distance information, visible or audible warnings (e.g., "Target too close", "Target too far"), or similar. In addition, the processor 46 can be configured to automatically turn off the lasers 64 when oxygen saturation image capture starts.

The multispectral medical imaging device 10 is capable of assisting in determining a venous block and a venous and arterial block.

Figure 17:
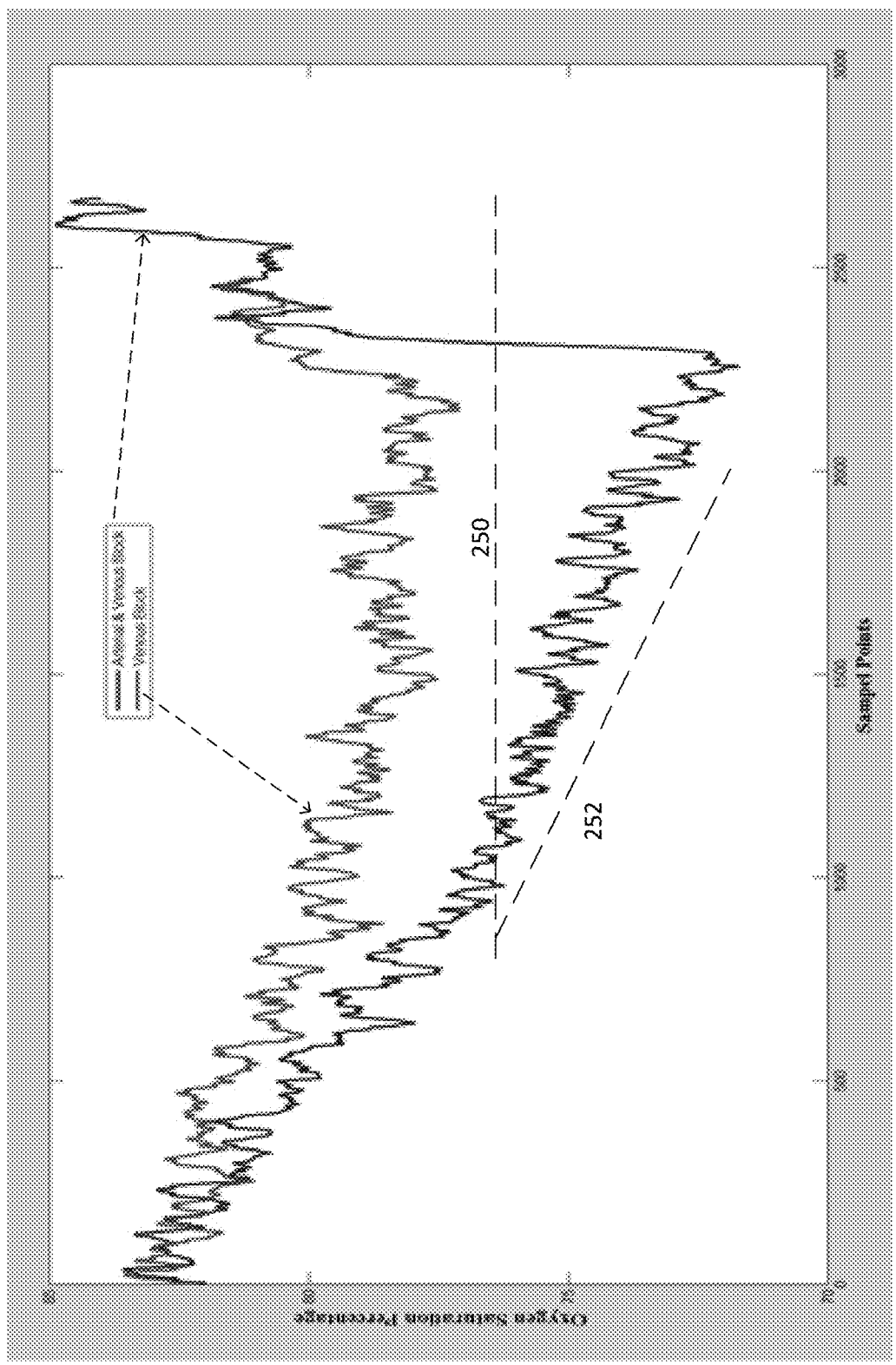
FIG. 17 is a chart showing the device response to a simulated venous block and a simulated arterial block.

FIG. 17 shows a chart of rates of desaturation of hemoglobin, as calculated by device 10, for a simulated venous block and a simulated venous and arterial block. The x-axis is sample points, representative of time, and the y-axis is oxygen saturation percentage.

As can be seen, a venous block exhibits a slower rate of oxygen desaturation, whereas a venous and arterial block exhibits a higher rate of desaturation. The venous block also does not reach as low a level of oxygen saturation as does the venous and arterial block.

The device 10 can be configured with a selectable threshold level 250 to assist in differentiating between a venous block and a venous and arterial block. Additionally or alternatively, the device 10 can be configured to calculate and selectably output a chart of oxygen saturation over time, similar to shown, for the target tissue 24 as a whole, to permit a clinician to view such and compare such to a selectable threshold level 250, if provided. One or more reference slopes 252 may also be provided to assist the clinician in assessing desaturation rate.

The device 10 can be configured to provide for selection of a block test duration, such as 45 seconds, 1 minute, etc.

The multispectral medical imaging device 10 is capable of detecting water content in the target tissue. The device may thus also be configured to detect a venous block by detecting increased water retention caused by a venous block in the region of interest.

In view of the above, numerous advantages of the present invention should be apparent to those skilled in the art. The techniques discussed herein provide for large-area multispectral imaging, dynamically in real time or near real time. Video frame rates can be achieved without moving parts. Compensation is provided for ambient lighting, patient skin tone, curvature, and the presence of vasculature. The invention also provides for aiming the device at the correct focal distance and towards an area of interest, in a convenient and repeatable manner. In addition, useful supplemental features, such as temporal difference visualization of oxygen desaturation and venous/arterial block detection, are provided.

While the foregoing provides certain non-limiting example embodiments, it should be understood that combinations, subsets, and variations of the foregoing are contemplated. The monopoly sought is defined by the claims.

What is claimed is:

1. A multispectral medical imaging device comprising:
  a plurality of illumination devices arranged to illuminate a target tissue, the plurality of illumination devices comprising near-infrared illumination devices configured to emit light of different near-infrared wavelength bands and a visible-light illumination device configured to emit visible light to illuminate the target tissue;
  an objective lens;
  a near-infrared image sensor positioned to sequentially capture image frames of near-infrared light reflected from the target tissue through the objective lens;
  a visible-light image sensor positioned to capture image frames of visible light reflected from the target tissue through the objective lens;
  an image capture buffer coupled to the near-infrared image sensor and the visible-light image sensor, the image capture buffer configured to store the image frames sequentially captured by the near-infrared image sensor and the image frames captured by the visible-light image sensor;
  a processor connected to the near-infrared image sensor, the visible-light image sensor, the plurality of illumination devices, and the image capture buffer, the processor configured to modulate near-infrared light output of the plurality of illumination devices to illuminate the target tissue by sequentially driving the near-infrared illumination devices to emit light of the different near-infrared wavelength bands, the processor further configured to:
    perform rolling processing on the image frames sequentially captured by the near-infrared image sensor that are stored in the image buffer to form output frames, each output frame comprising an image frame sequentially captured by the near-infrared image sensor for each one of the different near-infrared wavelength bands emitted by the near-infrared sensor;
    use the near-infrared image sensor to capture an ambient infrared image frame of the target tissue when controlling all of the illumination devices to not illuminate the target tissue;
    for each respective output frame, subtract the ambient infrared image frame from each image frame of the respective output frame;
    determine reflectance intensities from the image frames;
    perform delta processing on the reflective intensities for each one of the different near-infrared wavelength bands for each respective output frame to generate delta processed reflective intensities for each one of the different near-infrared wavelength bands for each respective output frame; and,
    combine the delta processed reflective intensities for each one of the different near-infrared wavelength bands for each respective output frame to generate a dynamic tissue oxygen saturation map of the target tissue; and an output device connected to the processor for displaying the dynamic tissue oxygen saturation map.

2. The device of claim 1, wherein the processor is configured to perform delta processing on the reflective intensities for each one of the different near-infrared wavelength bands for each respective output frame by comparing the reflectance intensities for each one of the different near-infrared wavelength bands for each respective output frame to a reference standard for each one of the different near-infrared wavelength bands.

3. The device of claim 1, wherein the plurality of illumination devices are arranged in a ring around the objective lens.

4. The device of claim 1, wherein the plurality of illumination devices comprises at least four near-infrared illumination devices having near-infrared wavelength bands with nominal peak wavelengths of 740, 780, 850 and 940 nm.

5. The device of claim 1, further comprising a dichroic beam splitter positioned between the objective lens and the near-infrared and visible-light image sensors, the dichroic beam splitter arranged to split light from the objective lens between the near-infrared and visible-light image sensors.

6. The device of claim 1, wherein the visible light illumination device comprises a white-light illumination device arranged to illuminate the target tissue with white light.

7. The device of claim 1, wherein the output device comprises a display for displaying the dynamic tissue oxygen saturation map on an image of the target tissue for viewing by a clinician.

8. The device of claim 1, wherein the output device comprises a projector positioned to project the dynamic tissue oxygen saturation map onto a skin surface over the target tissue.

9. The device of claim 1, wherein the processor is configured to periodically drive the visible-light illumination device to emit visible light to illuminate the target tissue.

10. The device of claim 9, wherein a frame rate of the dynamic tissue oxygen saturation map is equal to a combined frequency of modulation of all of the plurality of illumination devices.

11. The device of claim 1, wherein the processor is further configured to perform motion correction on the image frames captured by the near-infrared image sensor, the motion correction comprising selecting a reference frame from the image frames and calculating image registration coefficients for at least one subsequent image frame of the image frames.

12. The device of claim 11, wherein calculating image registration coefficients comprises performing a space transformation on the reference frame and the at least one subsequent image frame.

13. The device of claim 11, wherein calculating image registration coefficients comprises performing feature detection on the reference frame and the at least one subsequent image frame.

14. The device of claim 11, wherein the processor is further configured to calculate image registration coefficients for the motion correction using sub-regions of the image frames captured by the near-infrared image sensor, the sub-regions having dimensions smaller than a size of the image frames and being located away from edges of the image frames.

15. The device of claim 11, wherein the processor is further configured to perform motion correction on the visible-light image frames captured by the visible-light image sensor.

16. The device of claim 15, wherein the motion correction comprises performing feature detection including detection of an ink mark on a skin surface over the target tissue.

17. The device of claim 15, wherein the motion correction comprises performing feature detection including detection of body hair on skin over the target tissue.

18. The device of claim 17, wherein the motion correction comprises performing feature detection including detection of vasculature of the target tissue.

19. The device of claim 1, wherein the processor is further configured to use the visible-light image frames to determine a correction for melanin in skin over the target tissue and to apply the correction to the reflectance intensities determined from the image frames captured by the near-infrared image sensor.

20. The device of claim 19, wherein the processor is configured to determine the correction from a predetermined relationship between visible light reflected intensity determined from the visible light frames and melanin concentration.

21. The device of claim 1, wherein the processor is further configured to repeatedly capture ambient infrared image frames and, for each respective output frame, to subtract a most recent ambient infrared image frame from the image frames of the respective output frame.

22. The device of claim 1, wherein the processor is further configured to trigger capture of the ambient infrared image frame based on a change in ambient infrared illumination that exceeds a threshold.

23. The device of claim 22, further comprising an ambient-light sensor connected to the processor and configured to detect the change in ambient infrared illumination.

24. The device of claim 22, further comprising a visible-light image sensor connected to the processor and configured to detect a change in ambient visible illumination indicative of the change in ambient infrared illumination.

25. The device of claim 1, wherein the processor is further configured to mask a region of the dynamic tissue oxygen saturation map where intensities of the region in image frames of different near-infrared wavelength bands indicate a threshold amount of curvature of the target tissue.

26. The device of claim 1, wherein the processor is further configured to perform a temporal difference operation on a sequence of frames of the dynamic tissue oxygen saturation map with respect to a reference frame of the dynamic tissue oxygen saturation map.

27. The device of claim 1, wherein the processor is further configured to use the image frames to calculate a rate of desaturation of hemoglobin in the target tissue over a period of time for determining a venous or arterial blockage.

28. The device of claim 1, wherein the processor is further configured to use the image frames to identify veins in the target tissue and to modify reflectance intensities to compensate for oxygenation or deoxygenating at the veins when generating the dynamic tissue oxygen saturation map.

29. The device of claim 1, further comprising at least one laser positioned to emit a plurality of laser points onto a skin surface over the target tissue, the laser points for assisting manual positioning of the device with respect to the target tissue.

30. The device of claim 29, further comprising a visible-light image sensor connected to the processor for capturing light from the laser points reflected from the skin surface, the processor further configured to include the laser points in the dynamic tissue oxygen saturation map.

31. The device of claim 29, wherein the at least one laser is configured to emit the plurality of laser points at a near-infrared wavelength band detectable by the near-infrared image sensor to include the laser points in the dynamic tissue oxygen saturation map.

32. The device of claim 29, further comprising optics configured to emit lines of laser light onto the skin surface over the target tissue, the lines of laser light including the laser points.

33. The device of claim 32, wherein the lines of laser light are arranged as a rectangular box.

34. The device of claim 1, further comprising:
   a first positioning laser positioned at a first offset distance from an optical axis of the objective lens and aimed at a first angle with respect to the optical axis to emit a first positioning laser spot on a skin surface over the target tissue; and
   a second positioning laser positioned at a second offset distance from the optical axis of the objective lens and aimed at a second angle with respect to the optical axis to emit a second positioning laser spot on the skin surface;
   the first and second angles laying in different planes that contain the optical axis, and the first and second offset distances and angles are selected to cause the first positioning laser spot and the second positioning laser spot to be coincident at the optical axis when the target tissue is a target distance from the objective lens.

35. The device of claim 34, wherein the first and second offset distances and angles are configured to position the first and second positioning laser spots on one side of the optical axis of the objective lens when a distance from the objective lens to the target tissue is greater than the target distance and to position the first and second positioning laser spots on an opposite side of the target when the distance from the objective lens to the target tissue is less than the target distance.

36. The device of claim 34, wherein the first and second positioning lasers are positioned at about 90 degrees apart on a circle centered at the optical axis of the objective lens.

37. The device of claim 1, wherein the processor is further configured to align the image frames captured by the visible-light image sensor with the image frames captured by the near-infrared image sensor using displacement coefficients stored in memory, the displacement coefficients being predetermined based on image registration performed on at least one standard image captured by both of the near-infrared image sensor and the visible-light image sensor.

* * * * *